United States Patent
Nicoud et al.

(10) Patent No.: US 9,150,816 B2
(45) Date of Patent: Oct. 6, 2015

(54) CHROMATOGRAPHIC METHOD FOR THE PRODUCTION OF POLYUNSATURATED FATTY ACIDS

(71) Applicant: Novasep Process SAS, Pompey (FR)

(72) Inventors: Roger-Marc Nicoud, Lay-Saint-Christophe (FR); Jean Bléhaut, Nancy (FR)

(73) Assignee: Novasep Process SAS, Pompey (FR)

( * ) Notice: Subject to any disclaimer, the term of this patent is extended or adjusted under 35 U.S.C. 154(b) by 0 days.

(21) Appl. No.: 14/520,856

(22) Filed: Oct. 22, 2014

(65) Prior Publication Data

US 2015/0158804 A1 Jun. 11, 2015

(30) Foreign Application Priority Data

Dec. 11, 2013 (EP) .................................. 13306701

(51) Int. Cl.
| | |
|---|---|
| *C11B 7/00* | (2006.01) |
| *C07C 51/48* | (2006.01) |
| *C07C 57/02* | (2006.01) |
| *C11C 1/00* | (2006.01) |

(52) U.S. Cl.
CPC .............. *C11B 7/0008* (2013.01); *C11B 7/0025* (2013.01); *C07C 51/48* (2013.01); *C07C 57/02* (2013.01); *C11C 1/005* (2013.01); *C11C 1/007* (2013.01)

(58) Field of Classification Search
None
See application file for complete search history.

(56) References Cited

U.S. PATENT DOCUMENTS

| | | | |
|---|---|---|---|
| 2,985,589 | A | 5/1961 | Broughton et al. |
| 3,696,107 | A | 10/1972 | Neuzil |
| 3,706,812 | A | 12/1972 | deRosset et al. |
| 3,761,533 | A | 9/1973 | Otani et al. |
| 4,036,745 | A | 7/1977 | Broughton |

(Continued)

FOREIGN PATENT DOCUMENTS

| | | |
|---|---|---|
| DK | 1338316 T3 | 3/2005 |
| DK | 1128881 T3 | 10/2005 |

(Continued)

OTHER PUBLICATIONS

Yamamura, R. et al., Industrial High-Performance liquid chromatography purification of docosahexaenoic acid ethyl ester and docosapentaenoic acid ethyl ester from single-cell oil, 1997, JAOCS, vol. 74, No. 11, pp. 1435-1440.*

(Continued)

*Primary Examiner* — Yate K Cutliff
(74) *Attorney, Agent, or Firm* — Harness, Dickey & Pierce, P.L.C.

(57) ABSTRACT

A method for purification of a first polyunsaturated fatty acid from an initial mixture is provided. The initial mixture comprises at least one second fatty acid in addition to the first polyunsaturated fatty acid. The method may comprise separating the first polyunsaturated fatty acid and the second fatty acid in a liquid phase in at least one step of a chromatographic separation process, so as to recover, on the one hand, a stream enriched in the first polyunsaturated fatty acid, and on the other hand, a stream enriched in the second fatty acid. The method may further comprise a step of processing the stream enriched in the first polyunsaturated fatty acid to decrease the peroxide value and/or anisidine value of this stream. The disclosure also provides systems or devices suitably adapted for the implementation of such methods.

29 Claims, 1 Drawing Sheet

(56) References Cited

U.S. PATENT DOCUMENTS

| | | |
|---|---|---|
| 4,048,111 A | 9/1977 | Rosback et al. |
| 4,048,205 A | 9/1977 | Neuzil et al. |
| 4,049,688 A | 9/1977 | Neuzil et al. |
| 4,189,422 A | 2/1980 | Wakeford |
| 4,189,442 A | 2/1980 | Lubsen et al. |
| 4,313,015 A | 1/1982 | Broughton |
| 4,329,280 A | 5/1982 | Cleary et al. |
| 4,353,838 A | 10/1982 | Cleary et al. |
| 4,353,839 A | 10/1982 | Cleary et al. |
| 4,404,145 A | 9/1983 | Cleary et al. |
| 4,433,195 A | 2/1984 | Kulprathipanja |
| 4,460,675 A | 7/1984 | Gruetzmacher et al. |
| 4,486,618 A | 12/1984 | Kulprathipanja et al. |
| 4,495,106 A | 1/1985 | Cleary et al. |
| 4,497,710 A * | 2/1985 | Wagu et al. .................. 210/635 |
| 4,511,514 A | 4/1985 | Cleary et al. |
| 4,519,952 A | 5/1985 | Cleary et al. |
| 4,521,343 A | 6/1985 | Chao et al. |
| 4,522,761 A | 6/1985 | Cleary et al. |
| 4,524,029 A | 6/1985 | Cleary et al. |
| 4,524,030 A | 6/1985 | Cleary et al. |
| 4,529,551 A | 7/1985 | Cleary et al. |
| 4,560,675 A | 12/1985 | Cleary et al. |
| 4,605,783 A | 8/1986 | Zinnen |
| 4,720,579 A | 1/1988 | Kulprathipanja |
| 4,764,276 A | 8/1988 | Berry et al. |
| 4,797,233 A | 1/1989 | Zinnen |
| 4,882,065 A | 11/1989 | Barder |
| 4,902,829 A | 2/1990 | Kulprtahipanja |
| 4,961,881 A | 10/1990 | Ou |
| 5,064,539 A | 11/1991 | Tanimura et al. |
| 5,068,418 A | 11/1991 | Kulprathipanja et al. |
| 5,068,419 A | 11/1991 | Kulprathipanja et al. |
| 5,069,883 A | 12/1991 | Matonte |
| 5,093,004 A | 3/1992 | Hotier et al. |
| 5,102,553 A | 4/1992 | Kearney et al. |
| 5,114,590 A | 5/1992 | Hotier et al. |
| 5,179,219 A | 1/1993 | Priegnitz |
| 5,225,580 A | 7/1993 | Zinnen |
| 5,405,534 A | 4/1995 | Ishida et al. |
| 5,422,007 A | 6/1995 | Nicoud et al. |
| 5,502,077 A | 3/1996 | Breivik et al. |
| 5,547,580 A * | 8/1996 | Tsujii et al. .................. 210/656 |
| 5,630,943 A | 5/1997 | Grill |
| 5,656,667 A | 8/1997 | Breivik et al. |
| 5,698,594 A | 12/1997 | Breivik et al. |
| 5,719,302 A * | 2/1998 | Perrut et al. .................. 554/191 |
| 5,777,141 A | 7/1998 | Brunner et al. |
| 5,790,181 A | 8/1998 | Chahl et al. |
| 5,840,181 A | 11/1998 | Patton et al. |
| 5,840,944 A | 11/1998 | Furihata et al. |
| 5,917,068 A | 6/1999 | Barnicki et al. |
| 5,945,318 A * | 8/1999 | Breivik et al. .................. 435/134 |
| 6,013,186 A | 1/2000 | Patton et al. |
| 6,063,284 A | 5/2000 | Grill |
| 6,096,218 A | 8/2000 | Hauck et al. |
| 6,136,198 A | 10/2000 | Adam et al. |
| 6,204,401 B1 | 3/2001 | Perrut et al. |
| 6,306,306 B1 | 10/2001 | Voigt et al. |
| 6,313,330 B1 | 11/2001 | Kiyohara et al. |
| 6,325,598 B1 | 12/2001 | Sud et al. |
| 6,325,898 B1 | 12/2001 | Blehaut et al. |
| 6,350,890 B1 | 2/2002 | Kiy et al. |
| 6,375,839 B1 | 4/2002 | Adam et al. |
| 6,384,077 B1 * | 5/2002 | Peet et al. .................. 514/560 |
| 6,409,923 B1 | 6/2002 | Nicoud et al. |
| 6,413,419 B1 | 7/2002 | Adam et al. |
| 6,433,201 B2 * | 8/2002 | Fujita et al. .................. 554/191 |
| 6,471,870 B1 | 10/2002 | Nicoud et al. |
| 6,518,049 B1 | 2/2003 | Haraldsson et al. |
| 6,544,413 B1 | 4/2003 | Nagamatsu et al. |
| 6,675,839 B1 | 1/2004 | Braithwaite |
| 6,712,973 B2 | 3/2004 | Adam et al. |
| 6,713,447 B2 | 3/2004 | Beaudoin et al. |
| 6,740,243 B2 | 5/2004 | Wankat |
| 6,789,502 B2 | 9/2004 | Hjaltason et al. |
| 6,863,824 B2 | 3/2005 | Hamende et al. |
| 6,979,402 B1 | 12/2005 | Sprague et al. |
| 7,063,855 B2 | 6/2006 | Hjaltason et al. |
| 7,462,643 B1 | 12/2008 | Pamparana |
| 7,479,228 B2 | 1/2009 | Schramm et al. |
| 7,491,522 B2 | 2/2009 | Haraldsson et al. |
| 7,541,480 B2 | 6/2009 | Bruzzese |
| 7,588,791 B2 * | 9/2009 | Fabritius .................. 426/601 |
| 7,667,061 B2 | 2/2010 | Binder et al. |
| 7,678,930 B2 | 3/2010 | Sondbo et al. |
| 7,705,170 B2 | 4/2010 | Geier et al. |
| 7,709,236 B2 | 5/2010 | Akimoto et al. |
| 7,718,698 B2 | 5/2010 | Breivik et al. |
| 7,732,488 B2 | 6/2010 | Breivik et al. |
| 7,807,848 B2 | 10/2010 | Wang |
| 7,901,581 B2 | 3/2011 | Bryntesson et al. |
| 8,063,235 B2 * | 11/2011 | Krumbholz et al. .......... 554/191 |
| 8,216,475 B2 | 7/2012 | Valery et al. |
| 8,282,831 B2 | 10/2012 | Kessler et al. |
| 8,802,880 B1 * | 8/2014 | Adam et al. .................. 554/193 |
| 2001/0025112 A1 * | 9/2001 | Fujita et al. .................. 554/191 |
| 2002/0011445 A1 | 1/2002 | Lehoucq et al. |
| 2002/0068833 A1 | 6/2002 | Chanteloup et al. |
| 2002/0174769 A1 | 11/2002 | Adam et al. |
| 2003/0006191 A1 | 1/2003 | Heikkila et al. |
| 2003/0216543 A1 | 11/2003 | Wang et al. |
| 2003/0222024 A1 | 12/2003 | Hamende et al. |
| 2004/0099604 A1 | 5/2004 | Hauck et al. |
| 2005/0087494 A1 | 4/2005 | Hauck et al. |
| 2005/0245405 A1 | 11/2005 | Geier et al. |
| 2006/0008667 A1 | 1/2006 | Kim et al. |
| 2006/0086667 A1 | 4/2006 | Hauck et al. |
| 2006/0124549 A1 | 6/2006 | Bailly et al. |
| 2007/0068873 A1 | 3/2007 | Oroskar et al. |
| 2007/0148315 A1 | 6/2007 | Schaap et al. |
| 2007/0158270 A1 | 7/2007 | Geier et al. |
| 2007/0181504 A1 | 8/2007 | Binder et al. |
| 2008/0234375 A1 | 9/2008 | Breivik et al. |
| 2009/0023808 A1 | 1/2009 | Raman et al. |
| 2009/0176284 A1 | 7/2009 | Furihata et al. |
| 2010/0012584 A1 | 1/2010 | Majewski et al. |
| 2010/0069492 A1 * | 3/2010 | Geiringen et al. .......... 514/560 |
| 2010/0104657 A1 | 4/2010 | Sondbo et al. |
| 2010/0160435 A1 | 6/2010 | Bruzzese |
| 2010/0163490 A1 | 7/2010 | Lasalle |
| 2010/0186587 A1 | 7/2010 | Kessler et al. |
| 2010/0190220 A1 * | 7/2010 | Furihata et al. .......... 435/134 |
| 2010/0197785 A1 | 8/2010 | Breivik |
| 2010/0233281 A1 | 9/2010 | Breivik et al. |
| 2010/0267829 A1 | 10/2010 | Breivik et al. |
| 2010/0331559 A1 | 12/2010 | Feist et al. |
| 2010/0331561 A1 | 12/2010 | Schaap et al. |
| 2011/0000853 A1 | 1/2011 | Valery et al. |
| 2011/0015418 A1 | 1/2011 | Krumbholz et al. |
| 2011/0030457 A1 | 2/2011 | Valery et al. |
| 2011/0091947 A1 * | 4/2011 | Kim et al. .................. 435/134 |
| 2011/0139001 A1 | 6/2011 | Hilaireau et al. |
| 2011/0168632 A1 | 7/2011 | Valery et al. |
| 2012/0214966 A1 | 8/2012 | Theoleyre et al. |
| 2012/0232141 A1 | 9/2012 | Hustvedt et al. |
| 2012/0309995 A1 | 12/2012 | Arhancet et al. |
| 2012/0330043 A1 | 12/2012 | Kelliher et al. |
| 2014/0128627 A1 * | 5/2014 | Kelliher et al. .......... 554/207 |
| 2014/0336400 A1 | 11/2014 | Adam et al. |

FOREIGN PATENT DOCUMENTS

| | | |
|---|---|---|
| EP | 0255824 A1 | 2/1988 |
| EP | 0292846 A2 | 11/1988 |
| EP | 0342629 B1 | 8/1993 |
| EP | 0697034 A1 | 2/1996 |
| EP | 0773283 A2 | 5/1997 |
| EP | 0981399 A1 | 3/2000 |
| EP | 1106602 A1 | 6/2001 |
| EP | 1128881 A1 | 9/2001 |
| EP | 1152755 A1 | 11/2001 |
| EP | 1157692 A1 | 11/2001 |
| EP | 1166840 A1 | 1/2002 |

(56) References Cited

FOREIGN PATENT DOCUMENTS

| | | |
|---|---|---|
| EP | 1250058 A1 | 10/2002 |
| EP | 1250059 A2 | 10/2002 |
| EP | 1392411 A1 | 3/2004 |
| EP | 1436370 A1 | 7/2004 |
| EP | 1523541 A1 | 4/2005 |
| EP | 1534807 A1 | 6/2005 |
| EP | 1685222 A1 | 8/2006 |
| EP | 1749079 A1 | 2/2007 |
| EP | 1982752 A1 | 10/2008 |
| EP | 2169038 A1 | 3/2010 |
| EP | 2173184 A1 | 4/2010 |
| EP | 2173699 A1 | 4/2010 |
| EP | 2295529 A2 | 3/2011 |
| EP | 2591778 A1 | 5/2013 |
| FR | 2103302 A5 | 4/1972 |
| FR | 2651148 A1 | 3/1991 |
| FR | 2651149 A1 | 3/1991 |
| FR | 2785196 A1 | 5/2000 |
| FR | 2889077 A1 | 2/2007 |
| FR | 2897238 A1 | 8/2007 |
| GB | 2221843 A | 2/1990 |
| HK | 1078509 A1 | 6/2006 |
| JP | 5888339 A | 5/1983 |
| JP | 58109444 A | 6/1983 |
| JP | 60197209 A | 10/1985 |
| JP | 61-192797 A | 8/1986 |
| JP | H01197596 A | 8/1989 |
| JP | H04235701 A | 8/1992 |
| JP | 05168434 A | 7/1993 |
| JP | 05171177 A | 7/1993 |
| JP | 06287594 A | 10/1994 |
| JP | 08218091 A | 8/1996 |
| JP | 08512336 A | 12/1996 |
| JP | 09157684 A | 6/1997 |
| JP | H10310555 A | 11/1998 |
| JP | 11-57302 A | 3/1999 |
| JP | 11-90105 A | 4/1999 |
| JP | H11209785 A | 8/1999 |
| JP | 2001139981 A | 5/2001 |
| JP | 2010530068 A | 9/2010 |
| SI | 1797021 T1 | 4/2009 |
| WO | 87/03899 A1 | 7/1987 |
| WO | 94/25552 A1 | 11/1994 |
| WO | 98/32514 A1 | 7/1998 |
| WO | 98/51391 A1 | 11/1998 |
| WO | 99/47228 A1 | 9/1999 |
| WO | 00/25885 A1 | 5/2000 |
| WO | 00/48592 A1 | 8/2000 |
| WO | 01/50880 A2 | 7/2001 |
| WO | 01/50884 A1 | 7/2001 |
| WO | 01/87451 A2 | 11/2001 |
| WO | 01/87452 A2 | 11/2001 |
| WO | 01/87924 A2 | 11/2001 |
| WO | 02/089946 A1 | 11/2002 |
| WO | 03/033631 A1 | 4/2003 |
| WO | 2004/007654 A1 | 1/2004 |
| WO | 2004/007655 A1 | 1/2004 |
| WO | 2005/049772 A1 | 6/2005 |
| WO | 2005/100519 A1 | 10/2005 |
| WO | 2007/012750 A2 | 2/2007 |
| WO | 2007/017240 A2 | 2/2007 |
| WO | 2007/038417 A2 | 4/2007 |
| WO | 2007/075499 A2 | 7/2007 |
| WO | 2007/093690 A1 | 8/2007 |
| WO | 2007/147554 A2 | 12/2007 |
| WO | 2008/004900 A1 | 1/2008 |
| WO | 2008/107562 A2 | 9/2008 |
| WO | 2008/149177 A2 | 12/2008 |
| WO | 2009/006317 A1 | 1/2009 |
| WO | 2009/014452 A1 | 1/2009 |
| WO | 2009/047408 A1 | 4/2009 |
| WO | 2009/105351 A1 | 8/2009 |
| WO | 2010/018423 A1 | 2/2010 |
| WO | 2010/119319 A1 | 10/2010 |
| WO | 2011/080503 A2 | 7/2011 |
| WO | 2013/005046 A1 | 1/2013 |
| WO | 2013/005047 A1 | 1/2013 |
| WO | 2013/005048 A1 | 1/2013 |
| WO | 2013/005051 A1 | 1/2013 |
| WO | 2013/005052 A1 | 1/2013 |
| WO | WO2013/005048 A1 * | 1/2013 | ............ B01D 15/18 |
| WO | WO2013/005051 A1 * | 1/2013 | ............ B01D 15/18 |
| ZA | 8905758 A | 4/1990 |

OTHER PUBLICATIONS

Alkio, M. et al., Purification of polyunsaturated fatty acid esters from tuna oil with supercritical fluid chromatography, 2000, JAOCS, vol. 77, No. 3, pp. 315-321.*

Cremasco, M. A., et al.; "Experimental Purification of Paclitaxel From a Complex Mixture of Taxanes Using a Simulated Moving Bed", Brazilian Journal of Chemical Engineering, vol. 26, No. 1, Jan.-Mar. 2009, pp. 207-218.

Dolan, John W.; "Temperature selectivity in reversed-phase high performance liquid chromatography", Journal of Chromatography A., 965, 2002, pp. 195-205.

Beebe, Janet M., et al., "Analytical-Scale High-Performance Liquid Chromatography of Omega-3 Fatty Acid Esters Derived From Fish Oils," Journal of Chromatography, vol. 468, pp. 225-233 (1989).

Beebe, Janet M., et al., "Preparative-Scale High-Performance Liquid Chromatography of Omega-3 Polyunsaturated Fatty Acid Esters Derived From Fish Oil," Journal of Chromatography, vol. 459, pp. 369-378 (1988).

Guiochon, et al., "Chapter 17.8.5 Multicomponent Separations in SMB," Fundamentals of Preparative and Non-Linear Chromatography, 2nd Ed., pp. 833-835 (2006).

Heinisch, Sabine, et al.; "Sense and nonsense of high-temperature liquid chromatography", Journal of Chromatography A., 1216, 2009, pp. 642-658.

Hidajat, K., et al., "Preparative-scale liquid chromatographic separation of ?-3 fatty acids from fish oil sources," Journal of Chromatography A, vol. 702, pp. 215-221 (1995).

Hur, Jin Seok, et. al.; "New Design of Simulated Moving Bed (SMB) for Ternary Separations", Ind. Eng. Chem. Res., 44(6), 2005, pp. 1906-1913.

Keßller, Lars Christian, et al.; "Theoretical study of multicomponent continuous countercurrent chromatography based on connected 4-zone units", Journal of Chromatography A., 1126, 2006, pp. 323-337.

Kim, Jeung Kun, et al., "Designs of Simulated-Moving-Bed Cascades for Quaternary Separations," Ind. Eng. Chem. Res., vol. 43, pp. 1071-1080 (2004) (published online Jan. 20, 2004).

Krzynowek, Judith, et al.; "Purification of Omega-3 Fatty Acids From Fish Oils Using HPLC: An Overview", Proceedings of the first joint conference of the Tropical and Subtropical Fisheries Technological Society of the Americas with the Atlantic Fisheries Technological Society, 1987, pp. 74-77.

Lee, Chong Ho, et al.; "Designs of simulated moving bed systems with less than N-1 cascades", Theories and Applications of Chem. Eng., vol. 9, No. 2, 2003, pp. 1949-1952.

Lee, Kwangnam, "Two-Section Simulated Moving-Bed Process," Separation Science and Technology, vol. 35, No. 4, pp. 519-534 (2000).

Medina, A. Robles, et al., "Concentration and Purification of Stearidonic, Eicosapentaenoic, and Docosahexaenoic Acids from Cod Liver Oil and the Marine Microalga Isochlysis galbana," Journal of the American Oil Chemists' Society, vol. 72, No. 5, pp. 575-583 (1995).

Mun, Sungyong, et al.; "Optimal Design of a Size-Exclusion Tandem Simulated Moving Bed for Insulin Purification", Ind. Eng. Chem. Res., 42(9), 2003, pp. 1977-1993.

Nicolaos, Alexandre, et al.; "Application of equilibrium theory to ternary moving bed configurations (four+four, five+four, eight and nine zones): I. Linear case", Journal of Chromatography A., 908, 2001, pp. 71-86.

Nicolaos, Alexandre, et al.; "Application of the equilibrium theory to ternary moving bed configurations (4+4, 5+4, 8 and 9 zones): II. Langmuir case", Journal of Chromatography A., 908, 2001, pp. 87-109.

(56) References Cited

OTHER PUBLICATIONS

Nicoud, R. M.; "Chapter 13: Simulated Moving-Bed Chromatography for Biomolecules", Separation Science and Technology, vol. 2, 2000, pp. 475-509.
Nicoud, Roger M.; "Chapter 1: Simulated Moving Bed (SMB): Some Possible Applications for Biotechnology", Bioseparation and Bioprocessing: A Handbook, vol. I: Biochromatography, Membrane Separations, Modeling, Validation, 1998, pp. 1-39.
Snyder, Lloyd R., et al.; "Chapter 6: Reversed-Phase Chromatography for Neutral Samples," Introduction to Modern Liquid Chromatography, Third Edition, 2010, pp. v-xxix and 253-301.
Szepesy, L., et al.; "Continuous Liquid Chromatography", Journal of Chromatography, 108, 1975, pp. 285-297.
Wolcott, R. G., et al.; "Computer simulation for the convenient optimization of isocratic reversed-phase liquid chromatographic separations by varying temperature and mobile phase strength", Journal of Chromatography A., 869, 2000, pp. 3-25.
Xie, Yi, et al.; "Standing Wave Design and Experimental Validation of a Tandem Simulated Moving Bed Process for Insulin Purification", Biotechnology Progress, 18(6), 2002, pp. 1332-1344.
Yamamura, R., et al.: "Industrial High-Performance Liquid Chromatography Purification of Docosahexaenoic Acid Ethyl Ester and Docosapentaenoic Acid Ethyl Ester from Single-Cell Oil", Journal of the American Oil Chemists' Society, vol. 74, No. 11, Jul. 30, 1997, pp. 1435-1440, XP002166746.

Yoo, Jong Shin, et al.; "Temperature-Programmed Microcolumn Liquid Chromatography/Mass Spectrometry", J. Microcol. Sep., 4(4), Sep. 4, 1992, pp. 349-362.
Zhang, Ziyang, et al., "PowerFeed operation of simulated moving bed units: changing flow-rates during the switching interval," Journal of Chromatography A, vol. 1006, pp. 87-99 (2003).
Zhu, Cuiru, et al.; "Elevated Temperature HPLC: Principles and Applications to Small Molecules and Biomolecules", LCGC Asia Pacific, vol. 8, No. 1, Mar. 2005, pp. 48-59.
Zhu, P. L., et al., "Combined use of temperature and solvent strength in reversed-phase gradient elution I. Predicting separation as a function of temperature and gradient conditions," Journal of Chromatography A, vol. 756, pp. 21-39 (1996).
Zhu, P. L., et al.; "Combined use of temperature and solvent strength in reversed-phase gradient elution: IV. Selectivity for neutral (non-ionized) samples as a function of sample type and other separation conditions", Journal of Chromatography A., 756, 1996, pp. 63-72.
Partial European Search Report dated Jan. 7, 2014 issued by the European Patent Office in related European App. No. 13305596.2.
Alkio, M. et al., Purification of polyunsaturated fatty acid esters from tuna oil with supercritical fluid chromatography, 2000, JAOCS, vol. 77, No. 3, pp. 315-321.
European Search Report dated May 8, 2014 issued by the European Patent Office in related European App. No. 13306701.7.
Torres C. F. et. al.; "Preparation of Purified Acylglycerols of Eicosapentaenoic Acid and Docosahexaenoic Acid and their Re-esterification with Conjugated Linoleic Acid," Enzyme and Microbial Technology, Stoneham, MA, US, vol. 32, Jan. 1, 2003, pp. 49-58.

\* cited by examiner

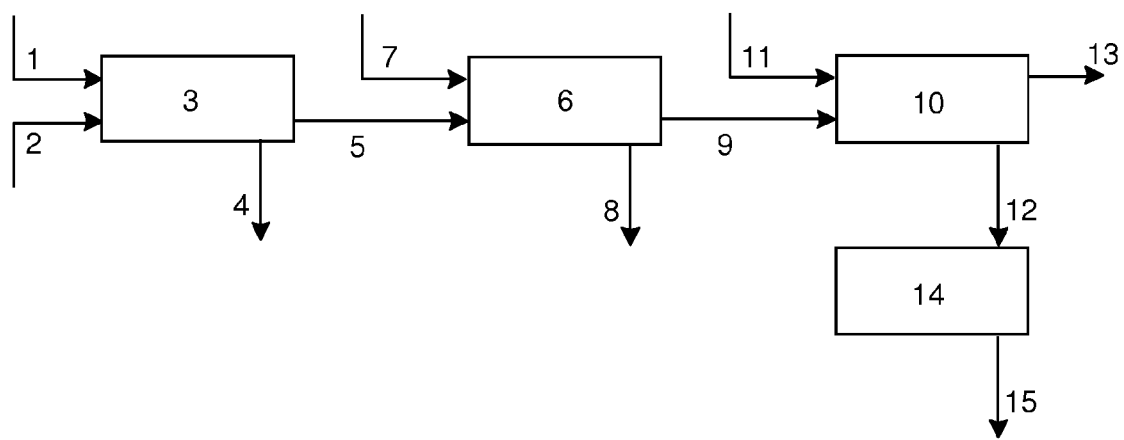

CHROMATOGRAPHIC METHOD FOR THE PRODUCTION OF POLYUNSATURATED FATTY ACIDS

CROSS-REFERENCE TO RELATED APPLICATION

This application claims the benefit and priority of European Patent Application EP13306701.7 filed on Dec. 11, 2013. The entire disclosure of the above application is incorporated herein by reference.

FIELD

The present disclosure relates to a chromatographic method for producing polyunsaturated fatty acids such as eicosapentaenoic acid, as well as to a system suitably adapted for the implementation of this method.

BACKGROUND

The citation of references herein does not constitute an admission that those references are prior art or have any relevance to the patentability of the technology disclosed herein.

Fatty acids, among which are included polyunsaturated fatty acids (abbreviated to PUFA), are particularly important biological compounds because they are involved in numerous biological processes such as building and maintenance of cell membranes, synthesis of hormones (for example, prostaglandins) that play a role in platelet aggregation, inflammation processes and in the human immunological response, etc.

The human body is able to synthesise most PUFAs, with the exception of two families of PUFAs known as essential fatty acids, which must necessarily be obtained through dietary intake.

The two families of essential fatty acids are:
- omega-6, which are particularly abundant in nut oils, and oils derived from sunflower, soybean, grapeseed or corn, and in fatty poultry (such as duck);
- omega-3 which are mostly found in nut oils, in plants such as rapeseed and flax, and in fatty fish (such as salmon, tuna, sardine, mackerel or herring). Omega-3 production processes using microalgae cultures, transgenic yeast or krill have recently been developed.

Omega-3s are PUFAs that are considered particularly interesting for their antioxidant properties. Among these omega-3s, purified EPA (eicosapentaenoic acid, C20-5ω3) and DHA (docosahexaenoic acid, C22-6ω3) and enriched combinations thereof are the most frequently used as dietary supplements or medicinal products to help lower blood triglyceride levels, reduce cardiovascular risks, and improve vision or cognitive functions, etc.

Recent clinical studies have shown that treatment of patients having triglyceride levels above 500 ml/dL with 4 grams per day of 96% EPA ethyl ester without DHA made it possible to lower triglyceride levels, without increasing the levels of low density lipoproteins or LDL ("bad" cholesterol), whereas treatment with 4 grams per day of a mixture of ethyl esters of EPA and DHA, in proportions of about 50% and 35%, respectively, led to an increase in LDL levels along with the concomitant decrease in triglyceride levels.

Up to the present time, the PUFA dietary supplements used, in particular omega-3s, have essentially been based on mixtures containing 30% to 60% of a mixture of EPA and DHA. In the separation methods used to date, the mixture is obtained by means of transesterification of triglycerides into ethyl esters and subsequently through the enrichment of omega-3s by means of molecular distillation and/or co-crystallisation of the saturated and mono-unsaturated fatty acids with urea. Eventually the enriched ethyl esters are possibly reconverted into triglycerides by means of a chemical or preferably enzymatic process.

However, these separation methods are not satisfactory for the production of an omega-3 such as EPA, DHA or even stearidonic acid (SDA, C18-Sω3) at more than 80%, or even more than 96%, especially in esterified form.

In fact, the purification of omega-3s is complex because these compounds comprise a plurality of carbon-carbon double bonds which make them sensitive to oxidation or degradation. In the presence of oxygen and when they are heated, these PUFAs undergo reactions including in particular isomerisation, oxidation, peroxidation and oligomerisation.

Thus, the separation techniques indicated here above are used to obtain a mixture of PUFA with a good yield and an acceptable degree of purity; but they cannot be implemented for the individual separation of PUFAs. They thus do not allow for the separation of omega-3s from each other. Indeed, molecular distillation, for example, cannot economically eliminate DHA from EPA or SDA; it does not provide for an efficient separation of long chain omega-3s particularly of the C20 and C22 types. The combination of clathration with urea and molecular distillation provides the ability to obtain omega-3 mixtures of higher purity, at the expense of yield which is generally lower, and at high operating cost, but may not be used for the separation of long chain omega-3s from one another, and of EPA and DHA in particular.

There is therefore a need to provide a process for the industrial purification of omega-3 in ultra high purity esterified form.

Chromatography is a fine separation technique that allows for the efficient purification or enrichment of molecules under mild conditions and protected from light and air.

This technology is based on the separation of molecules that are brought into contact with a stationary phase with which they have different interactions. The use of one or more fluids, referred to as mobile phases or eluents, enables the percolation of various different molecules at different speeds. These different speeds allow for the physical separation of molecules and enable them to be harvested in purified form upon completion of the chromatographic processes using one or more columns. The purified fractions are in general concentrated under mild conditions at ambient or moderate temperatures, by means such as vacuum evaporation or membrane processes.

In some cases, the feedstock for the chromatographic purification is an oil composed of esters of fatty acids already enriched by molecular distillation, preferably comprising more than 30% of the omega-3 of interest, which has undergone a treatment process for the removal of oxidised compounds, either by means of the last molecular distillation, or by adsorption, preferably on silica derivatives (silica gel, bentonite, diatomaceous earth) or on activated carbon, for example.

Numerous prior art documents describe the elimination of oxidised compounds from compositions derived from oils.

By way of example, EP 0682006 discloses a process for treating oils containing omega-3s by dilution in hexane and addition of 10% to 40% by weight of active charcoal.

U.S. Pat. No. 4,874,629 discloses a process for treating oils containing omega-3s by steam distillation followed by adsorption of polar compounds on silica.

WO 2005/049 772 also describes a process for treatment of an oil rich in omega-3 by dissolution in an aprotic solvent and contacting with a silicon derivative.

EP 0773283 describes a process for treatment of an oil containing a PUFA with at least 18 carbons by contacting for at least 10 minutes with a minimum of 0.1% by weight of a diatomaceous earth pre-treated in an acid medium at a temperature of optionally 5° C. to 80° C., followed or not by steam distillation.

A fair number of chromatographic methods have also been described, for obtaining an omega-3 with high purity.

Thus, U.S. Pat. No. 5,719,302 discloses a method in which the PUFAs are separated in particular by means of a supercritical eluant (carbon dioxide under pressure), and in particular on a "Simulated Moving Bed"—SMB.

US 2011/0091947 describes another process for purification of omega-3 using the technique of simulated moving bed chromatography. The document describes in particular the succession of one step of enzymatic transesterification, two steps of molecular distillation, and one step of the SMB type, these last three steps making it possible to separate the products into two fractions in order of retention time.

WO 2011/080503 describes the purification of omega 3 using a system comprising two SMB chromatography devices arranged in series and a washing zone, each SMB chromatography device defining one separation zone and consisting of multiple columns. The feedstock to be treated is injected into a first separation zone to obtain an extract stream and a raffinate stream, said raffinate stream containing the compounds of interest being then injected into a column of the second separation zone that is not adjacent to a column of the first zone.

WO 2013/005051 describes the purification of omega-3 by means of two chromatographic separation processes by SMB or AMB (that is to say, "Actual Moving Bed") in reversed phase mode with a water-organic eluent, wherein the two separations by SMB or AMB are performed sequentially on the same chromatographic device, or on two different devices, the intermediate purified by the first device being introduced into the second.

WO 2013/005048 describes the purification of EPA of over 90% purity by a first chromatographic separation followed by two chromatographic separations by SMB or AMB in reversed phase mode with a water-organic eluent in each step, the intermediate purified through the first chromatographic separation being introduced into the second chromatographic separation, and the intermediate purified through the second chromatographic separation being introduced into the third chromatographic separation.

In the two latter documents, the purified EPA is preferably obtained in the extract from the last separation; and thus the last separation separates EPA from the less retained impurities collected in the raffinate (as is well known to the person skilled in the art in reversed phase chromatography). Such impurities that are less retained than EPA may be, for example shorter chain PUFAs such as stearidonic acid (SDA), or oxidation compounds such as peroxides and aldehydes.

There is still a need to provide a PUFA (or a derivative thereof, in particular an ester thereof) with a high purity, allowing for its use in the preparation of medicinal compositions, from a multi compound feedstock including said PUFA. In particular, there is still a need to provide a PUFA (or a derivative thereof, in particular an ester thereof) that is essentially free of oxygenated contaminants such as peroxides or aldehydes.

SUMMARY

In certain aspects, a method for purification of a first polyunsaturated fatty acid from an initial mixture is provided, where the initial mixture comprising at least one second fatty acid in addition to the first polyunsaturated fatty acid, the method comprising:

at least one step of chromatographic separation in liquid phase of the first polyunsaturated fatty acid and the second fatty acid, so as to recover, on the one hand, a stream enriched in the first polyunsaturated fatty acid, and on the other hand, a stream enriched in the second fatty acid;

a step of processing the stream enriched in the first polyunsaturated fatty acid, so as to decrease the peroxide value and/or anisidine value of this stream.

According to one embodiment, the processing step is a step of molecular distillation.

According to one embodiment, the processing step is a step of contacting with an adsorption substrate, which is preferably selected from among silica, alumina, activated carbon and derivatives thereof; the contacting being carried out preferably without dilution of the first polyunsaturated fatty acid and without addition of a solvent.

According to one embodiment, the stream enriched in the first polyunsaturated fatty acid has, after the processing step, a peroxide value less than or equal to 10, preferably less than or equal to 5, or less than or equal to 2, or less than or equal to 1; and/or an anisidine value less than or equal to 20, preferably less than or equal to 10, or less than or equal to 5, or less than or equal to 3; and/or the stream enriched in the first unsaturated fatty acid has, prior to the processing step, a peroxide value greater than or equal to 1, preferably greater than or equal to 2, or greater than or equal to 4, or greater than or equal to 6, and/or an anisidine value greater than or equal to 1, preferably greater than or equal to 2, or greater than or equal to 4, or greater than or equal to 6.

According to one embodiment:

the first polyunsaturated fatty acid is eicosapentaenoic acid, and is preferably recovered after the process with a purity greater than or equal to: 80%, or 90%, or 96%; or the first polyunsaturated fatty acid is docosahexaenoic acid, and is preferably recovered after the process with a purity greater than or equal to: 70%, or 80%, or 90%, or 95%; or the first polyunsaturated fatty acid is arachidonic acid, and is preferably recovered after the process with a purity greater than or equal to: 70%, or 80%, or 90%, or 95%; or the first polyunsaturated fatty acid is docosapentaenoic acid, and is preferably recovered after the process with a purity greater than or equal to: 70%, or 80%, or 90%, or 95%.

According to one embodiment, the step of chromatographic separation of the first polyunsaturated fatty acid and the second fatty acid is implemented with a water-organic eluent.

According to one embodiment, the second fatty acid is a polyunsaturated fatty acid, preferably selected from among docosahexaenoic acid, eicosapentaenoic acid, arachidonic acid, stearidonic acid and docosapentaenoic acid.

According to one embodiment, the initial mixture further comprises a third fatty acid, and the method includes a step of liquid phase chromatographic separation of the first polyunsaturated fatty acid and the third fatty acid, so as to recover, on the one hand, a stream enriched in the first polyunsaturated fatty acid, and on the other hand, a stream enriched in the third fatty acid; this step of chromatographic separation being preferably carried out in certain variations with a water-organic eluent; and this step of chromatographic separation being preferably carried out upstream of the step of liquid phase chromatographic separation of the first polyunsaturated fatty acid and the second fatty acid.

According to one embodiment, the initial mixture further comprises a fourth fatty acid, and the method includes a step of liquid phase chromatographic separation of the first polyunsaturated fatty acid and the fourth fatty acid, so as to recover, on the one hand, a stream enriched in the first polyunsaturated fatty acid, and on the other hand, a stream enriched in the fourth fatty acid; this step of chromatographic separation being preferably carried out with a water-organic eluent; and this step of chromatographic separation being preferably carried out upstream of the step of liquid phase chromatographic separation of the first polyunsaturated fatty acid and the second fatty acid.

According to one embodiment:
  In certain aspects, the first polyunsaturated fatty acid is less retained than the second fatty acid during the step of chromatographic separation of the first polyunsaturated fatty acid and of the second fatty acid; and/or the first polyunsaturated fatty acid is less retained than the third fatty acid during the step of chromatographic separation of the first polyunsaturated fatty acid and of the third fatty acid; and/or the first polyunsaturated fatty acid is less retained than the fourth fatty acid during the step of chromatographic separation of the first polyunsaturated fatty acid and of the fourth fatty acid;
  In certain other aspects, preferably the first polyunsaturated fatty acid is less retained than two fatty acids selected from the second fatty acid, the third fatty acid and the fourth fatty acid, during the respective steps of chromatographic separation of the first polyunsaturated fatty acid and of the second, third and fourth fatty acid;
  In yet other aspects, in a particularly preferred manner, the method successively comprises (i) the step of liquid phase chromatographic separation of the first polyunsaturated fatty acid and the fourth fatty acid, the first polyunsaturated fatty acid being less retained than the fourth fatty acid, and then (ii) the step of liquid phase chromatographic separation of the first polyunsaturated fatty acid and the third fatty acid, the first polyunsaturated fatty acid being less retained than the third fatty acid, and then (iii) the step of liquid phase chromatographic separation of the first polyunsaturated fatty acid and the second fatty acid, the first polyunsaturated fatty acid being more retained than the second fatty acid.

According to one embodiment, the method includes a preliminary processing step so as to decrease the peroxide value and/or the anisidine value relative to the initial mixture, upstream of the liquid phase chromatographic separation step or steps, said preliminary processing step being preferably a molecular distillation step, or a step of contacting with an adsorption substrate, in particular selected from among silica, alumina, activated carbon and derivatives thereof.

In yet other aspects, a purification system is provided for purifying a first polyunsaturated fatty acid from an initial mixture, the system comprising:
  at least one unit for liquid phase chromatographic separation of the first polyunsaturated fatty acid and a second fatty acid, to which are connected at the outlet on the one hand, a line for a stream enriched in the first polyunsaturated fatty acid, and on the other hand, a line for a stream enriched in the second fatty acid;
  at least one processing unit fed by the line for the stream enriched in the first polyunsaturated fatty acid, the processing unit being adapted to bring about a decrease in the peroxide value and/or the anisidine value.

According to one embodiment, the processing unit is a molecular distillation unit; or a contacting unit for effecting contacting with an adsorption substrate, preferably selected from among silica, alumina, activated carbon and derivatives thereof; said contacting unit preferably not having any input of solvent.

According to one embodiment, the system comprises one unit for liquid phase chromatographic separation of the first polyunsaturated fatty acid and of a third fatty acid, and possibly one unit for liquid phase chromatographic separation of the first polyunsaturated fatty acid and of a fourth fatty acid, said liquid phase chromatographic separation units being preferably located upstream of the unit for liquid phase chromatographic separation of the first polyunsaturated fatty acid and second fatty acid.

According to one embodiment, at least one liquid phase chromatographic separation unit, preferably all of the liquid phase chromatographic separation units, are chromatographic separation units comprising a plurality of chromatographic separation columns, and preferably are simulated moving bed and/or real moving bed chromatographic separation units.

In certain aspects, the present teachings make it possible to overcome the disadvantages inherent in the techniques of the state of the art. It more particularly provides a method for obtaining a PUFA (or derivative thereof, in particular an ester thereof) of high purity and which may be used in the preparation of medicinal compositions, from a multi compound feedstock including the said PUFA. In particular, the PUFA thus obtained has a low level of, or is essentially free of oxygenated contaminants such as peroxides or aldehydes.

This is in part based on the finding by the inventors that the separation of an omega-3 by one or more steps of liquid phase chromatography, carried out in the absence of light and oxygen, in a surprising manner leads to an increase in the peroxide value and/or the anisidine value, such that an additional processing for eliminating oxidation compounds is necessary, even if the last chromatography step separates the desired omega-3 from less retained compounds.

More specifically, each time that the compound of interest is less retained than the compounds to be eliminated (collection at the raffinate, as part of a continuous process), the peroxide value and/or anisidine value increases, making an additional processing for elimination of the oxidation compounds necessary.

The presence of one or more steps in which the compound of interest is more retained than the compounds to be eliminated (collection at the extract, as part of a continuous process) may reduce the peroxide value and/or the anisidine value over the course of the process. However, it has been found that such a reduction is not necessarily sufficient, thus necessitating an additional processing for elimination of the oxidation compounds.

DRAWINGS

FIG. 1 represents an embodiment of a system for implementation of certain aspects of the present teachings in a schematic manner.

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

As used herein, the term "and/or" includes any and all combinations of one or more of the associated listed items.

Although the terms first, second, third, etc. may be used herein to describe various steps, elements, components, and/or features, these steps, elements, components, and/or features should not be limited by these terms, unless otherwise indicated. These terms may be only used to distinguish one step, element, component, or feature from another step, element, component, or feature. Terms such as "first," "second," and other numerical terms when used herein do not imply a sequence or order unless clearly indicated by the context. Thus, a first step, element, component, or feature discussed below could be termed a second step, element, component, or feature without departing from the teachings of the example embodiments.

Spatially or temporally relative terms, such as "before," "after," "inner," "outer," "beneath," "below," "lower," "above," "upper," and the like, may be used herein for ease of description to describe one element, component, or feature's relationship to another element(s), component(s), or feature(s) as illustrated in the FIGURE. Spatially or temporally relative terms may be intended to encompass different orientations of the device, component, or system in use or operation in addition to the orientation depicted in the figures, unless otherwise indicated.

It should be understood for any recitation of a method, composition, device, or system that "comprises" certain steps, ingredients, components, or features, that in certain alternative variations, it is also contemplated that such a method, composition, device, or system may also "consist essentially of" the enumerated steps, ingredients, components, or features, so that any other steps, ingredients, components, or features that would materially alter the basic and novel characteristics of the invention are excluded therefrom.

Throughout this disclosure, the numerical values represent approximate measures or limits to ranges to encompass minor deviations from the given values and embodiments having about the value mentioned as well as those having exactly the value mentioned. Other than in the working examples provided at the end of the Detailed Description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges.

Certain aspects of the present teachings will now be described in greater detail and in a non-limiting manner in the following description.

In a general manner, the proportions are expressed in weight proportions, unless otherwise stated.

General Principle Underlying the Method

In certain aspects, methods are provided that make it possible to obtain a first PUFA in purified form, from an initial mixture. The initial mixture comprises at least a second undesired fatty acid, which is preferably a second undesired PUFA, and preferably a certain number of other undesirable fatty acids, such as saturated or mono unsaturated fatty acids and other PUFAs, as well as other possible impurities.

The initial mixture may be a mixture of fatty acids derived from fish, plants, algae and/or yeast, and preferably from fish. It may be a raw material, for example fish oil or algae oil or yeast oil. It may also be a product derived from the above mentioned raw materials, and for example derived from fish oil, algae oil and/or oil yeast. The oil may for example be an extract from plants, algae or natural or genetically modified yeasts.

The term "product derived from a raw material" is understood to refer to a raw material which has been subjected to one or more processing steps. These processing steps may include one or more steps of cell disruption, grinding, separation or purification (for example fractionation) and/or a step of hydrolysis in order to convert triglycerides into free fatty acids and/or a step of esterification in order to convert fatty acids into alkyl esters and/or a step of transesterification in order to convert fatty triglycerides into alkyl esters and preferably into ethyl esters, and/or a step of reduction of the peroxide and/or the anisidine value (see below), and/or a step of molecular distillation, and/or one or more steps of chromatographic separation, etc.

According to a preferred embodiment, the initial mixture has a peroxide value lower than or equal to 15; or lower than or equal to 10; or lower than or equal to 8; or lower than or equal to 6; or lower than or equal to 5.

Furthermore, according to a preferred embodiment, the initial mixture has an anisidine value lower than or equal to 25; or lower than or equal to 20; or lower than or equal to 18; or lower than or equal to 15; or lower than or equal to 12, or lower than or equal to 10, or lower than or equal to 8, or lower than or equal to 6, or lower than or equal to 5.

This is generally made possible when the initial mixture is an oil product which has been subjected to a step of reduction of the peroxide and/or the anisidine value before the method according to certain aspects of the disclosure is implemented. This step can be performed in a similar way to what is described below in relation with the reduction of the peroxide and/or the anisidine value in the method according to certain aspects of the disclosure.

According to a preferred embodiment, the peroxide value and the anisidine value relative to the initial mixture, upstream of the liquid phase chromatographic separation step or steps comply with the specifications for the peroxide value and the anisidine value required for the purified first polyunsaturated fatty acid. In other words, the initial mixture, upstream of the liquid phase chromatographic separation step or steps has a predetermined peroxide value and a predetermined anisidine value in compliance with such specifications and required for the purified first polyunsaturated fatty acid.

According to an advantageous embodiment, the initial mixture is an esterified or transesterified product, such as a fish oil, a vegetable oil, an algae oil or a transesterified yeast oil.

Thus, each fatty acid (and in particular each PUFA) obtained or used in the method according to certain aspects of the disclosure may be a fatty acid derivative, in particular a monoglyceride, diglyceride or triglyceride, of: an ester, a phospholipid, an amide, a lactone or a salt.

The free fatty acid and ester forms are preferred, and most particularly the esters. The esters typically are alkyl esters, for example C1-C6 alkyl esters, in particular C1-C4 esters, such as methyl esters and ethyl esters. Ethyl esters are preferred.

Thus, the first PUFA, the second fatty acid, the third fatty acid and the fourth fatty acid mentioned in this present patent application may be for example in the form of free fatty acid or ester, and preferably are in the form of ethyl ester compounds.

With reference to FIG. 1, an exemplary method according to certain variations of the disclosure may be implemented in a system comprising a first chromatographic unit 10. The first chromatographic unit 10 performs the separation between the first PUFA and the second fatty acid.

Whenever mention is made in this present patent application of a separation between the first PUFA and a given fatty acid, it is understood that other fatty acids may also be separated from the first PUFA simultaneously with the separation with respect to the particular given fatty acid.

Generally, each chromatographic separation separates the first PUFA from a set of compounds that are more polar than it or less polar than it. The separation can also be carried out according to criteria such as size of aliphatic chain length and number of unsaturation. More generally, as the effects may be dependent upon the eluents used, the separation is carried out according to criteria of retention times which are different depending on the case, thereby allowing for the separating of the first PUFA from impurities which are more or less retained than itself.

The first chromatographic unit 10 is fed by a fatty acid mixture feeding line 9 as well as by an eluent feeding line 11. At the outlet of the first chromatographic unit 10 are connected on the one hand, a line of stream enriched in the first PUFA 12 and on the other hand, a line of stream enriched in the second fatty acid 13.

In the context of the present patent application, the term "enriched" has a relative meaning: a separation between a species A and a species B from an initial stream, so as to recover a stream enriched in species A, therefore means that the stream thus recovered has a weight ratio A/B that is greater than that of the initial stream.

The line of stream enriched in the first PUFA 12 supplies a first processing unit 14, which is adapted to bring about a reduction of the peroxide value and/or the anisidine value. At the outlet of the latter is connected a purified first PUFA collection line 15.

If the method has only one single chromatographic step, the other parts of the system shown in the FIGURE are omitted. In this case, the fatty acid mixture feeding line 9 supplies the first chromatographic unit 10 with the initial mixture (it being understood that this initial mixture may have been subjected to preliminary processing steps as described above, in which case the corresponding processing units, not shown, may be included in the system).

Alternatively, and as shown in the FIGURE, a second chromatographic unit 6 may be provided, in order to carry out a separation between the first PUFA and a third fatty acid. This second chromatographic unit 6 is supplied by a fatty acid mixture feeding line 5 as well as an eluent feeding line 7.

At the outlet of the second chromatographic unit 6 are connected on the one hand, a line of stream enriched in the first PUFA 9 and on the other hand, a line of stream enriched in the third fatty acid 8. The line of stream enriched in the first PUFA 9 constitutes the fatty acid mixture feeding line 9 for the first chromatographic unit 10.

If the method comprises of only two chromatographic steps, the other parts of the system shown in the FIGURE are omitted. In this case, the fatty acid mixture feeding line 5 supplies the second chromatographic unit 6 with the initial mixture (it being understood that this initial mixture may have been subjected to preliminary processing steps as described here above, in which case the corresponding processing units, not shown, may be included in the system).

Alternatively, and as shown in the FIGURE, a third chromatographic unit 3 may be provided, in order to carry out a separation between the first PUFA and a fourth fatty acid. This third chromatographic unit 3 is supplied fatty acid mixture feeding line 1 as well as an eluent feeding line 2.

At the outlet of the third chromatographic unit 3 are connected on the one hand, a line of stream enriched in the first PUFA 5 and on the other hand, a line of the stream enriched in the fourth fatty acid 4. The line of stream enriched in the first PUFA 5 constitutes the fatty acid mixture feeding line 5 for the second chromatographic unit 6.

If the method has three chromatographic steps, the fatty acid mixture feeding line 1 supplies the third chromatographic unit 3 with the initial mixture (it being understood that this initial mixture may have been subjected to preliminary processing steps as described here above, in which case the corresponding processing units, not shown, may be included in the system).

Alternatively, it may still be possible to provide for yet other similar chromatographic separation steps.

Thus, in the illustrated embodiment, the initial mixture is subjected to three successive steps of liquid phase chromatography:
 a step allowing for separating the first PUFA from the fourth fatty acid (in the third chromatographic unit 3);
 a step allowing for separating the first PUFA from the third fatty acid (in the second chromatographic unit 6);
 a step allowing for separating the first PUFA from the second fatty acid (in the first chromatographic unit 10)

Alternatively, the initial mixture undergoes only two successive steps of liquid phase chromatography:
 a step allowing for separating the first PUFA from the third fatty acid (in the second chromatographic unit 6);
 a step allowing for separating the first PUFA from the second fatty acid (in the first chromatographic unit 10).

Alternatively, the initial mixture undergoes one single step of liquid phase chromatography, that is to say, the separation of the first PUFA from the second fatty acid (in the first chromatographic unit 10).

Alternatively, the initial mixture is subjected to four successive steps of liquid phase chromatography:
- a step allowing for separating the first PUFA from a fifth fatty acid (in a chromatographic unit not shown);
- a step allowing for separating the first PUFA from the fourth fatty acid (in the third chromatographic unit 3);
- a step allowing for separating the first PUFA from the third fatty acid (in the second chromatographic unit 6);
- a step allowing for separating the first PUFA from the second fatty acid (in the first chromatographic unit 10).

Nature of the Chromatographic Separations

The term "chromatographic unit" is understood to refer to either a single column chromatographic system or a multi column chromatographic system.

Examples of single column chromatographic systems are the HPLC (High Performance Liquid Phase Chromatography) or CYCLOJET™ (chromatography system with Steady State Recycling) systems. Examples of multi column chromatographic systems include the following systems: SMB (Simulated Moving Bed), ISMB (Improved Simulated Moving Bed), AMB (Actual Moving Bed), VARICOL™, MODICON™, POWERFEED™, DCC (Dry Column Chromatography), MCSGP (Multicolumn Countercurrent Solvent Gradient Purification) and GSSR (multi column Gradient with Steady State Recycle).

The CYCLOJET™ system is as described in the patent document U.S. Pat. No. 6,063,284, the disclosure of which is explicitly incorporated herein by reference in its entirety. All references cited in the section of this specification are hereby incorporated by reference in their entirety. This is a system for single column batch chromatographic separation, in which the species (i) that are the most retained and then (ii) the least retained are collected separately at the outlet of the column, with a non-separated portion of the chromatogram being recycled by a main pump. The mixture to be separated is periodically injected by means of an injection loop in the recycled portion of the chromatogram. The injection loop is preferably connected between the main pump and the column. After several chromatographic runs, the process achieves a periodic stationary state wherein the quantity of products injected is equal to the quantity of products collected separately at the outlet of the column.

An SMB system comprises a plurality of individual columns containing an adsorbent, which are connected in series. An eluent stream passes through the columns in a first direction. The points of injection of the feed stream and the eluent, as well as the points of collection of the separated compounds, are periodically and simultaneously shifted by means of a valve assembly. The overall effect is to simulate the mode of operation of a single column containing a moving bed of solid adsorbent, the solid adsorbent moving in a counter current direction against the flow of the eluent stream. Thus, a SMB system consists of columns which contain stationary beds of solid adsorbent through which the eluent passes, but the operational mechanism is such that a continuous counter current moving bed is simulated.

The most conventional form of a SMB system is the four zone SMB system. Other possible forms are the three zone SMB systems and the two zone SMB systems (as described in the article "*Two Section Simulated Moving Bed Process*" by Kwangnam Lee in Separation Science and Technology 35 (4): 519-534, 2000, the disclosure of which is explicitly incorporated herein by reference in its entirety).

An iSMB system is as described in EP 0342629 and U.S. Pat. No. 5,064,539, the disclosures of which are explicitly incorporated herein by reference in their entireties. An SSMB system divides the introductions and collections of streams into subsequences applied in a periodic fashion. In the iSMB and SSMB systems, there is at least one step in which the system operates in a closed loop, without input or output of product.

Other variants of SMB systems are: the SMB system that is time varying and the POWERFEED™ system as described in U.S. Pat. No. 5,102,553 and in the article "*PowerFeed operation of simulated moving bed units: changing flow-rates during the switching interval*", by Zhang et al in Journal of Chromatography A, 1006:87-99, 2003, the disclosures of which are explicitly incorporated herein by reference in their entireties; the MODICON™ system, as described in U.S. Pat. No. 7,479,228, the disclosure of which is explicitly incorporated herein by reference in its entirety; and the SMB system with internal recirculation, as described in U.S. Pat. No. 8,282,831, the disclosure of which is explicitly incorporated herein by reference in its entirety.

An AMB system has a similar mode of operation to a SMB system. However, instead of displacing the points of injection of the feed stream and the eluent, as well as the points of collection, by means of a system of valves, a group of adsorption units (columns) are physically displaced relative to the supply and collection points. Once again, the mode of operation enables the simulation of a continuous counter current moving bed.

A VARICOL™ chromatography system is as described in U.S. Pat. No. 6,136,198, U.S. Pat. No. 6,375,839, U.S. Pat. No. 6,413,419 and U.S. Pat. No. 6,712,973, the disclosures of which are explicitly incorporated herein by reference in their respective entireties. A VARICOL™ system includes a plurality of individual columns containing an adsorbent, which are connected in series. An eluent is passed through the columns in a first direction. Unlike with the SMB system, the injection points for the mixture to be separated and for the eluent and points of collection of the compounds separated in the system are moved periodically but in an asynchronous manner, by means of a set of valves. The overall effect is to create separation zones of time varying length, thus allocating the stationary phase in a dynamic manner in the zones where it is most useful, and thereby providing for a similar power of separation with fewer chromatographic units and an increased level of productivity. Unlike an SMB system, a VARICOL™ system does not simulate the operation of a single column containing a moving bed of solid adsorbent, the solid adsorbent moving in a counter current direction against the flow of the eluent stream, and thus the operating principle of the VARICOL™ system cannot be implemented in an equivalent AMB system.

A DCC chromatography system is as described in FR 2889077, the disclosure of which is explicitly incorporated herein by reference in its entirety. A DCC system is a sequential process with periodic displacement of the points of injection of the mobile phase and the mixture to be separated, having the characteristic of being constantly in open loop. It uses two or more columns.

According to one embodiment, the method according to certain aspects of the disclosure comprises two successive steps of chromatographic separation (and only two), which may be AMB-, SMB-, or VARICOL™ separation steps.

According to one embodiment, the method according to certain aspects of the disclosure comprises three successive steps of chromatographic separation (and only three), which may be AMB-, SMB-, or VARICOL™ separation steps.

According to one embodiment, the method according to certain aspects of the disclosure comprises three successive steps of chromatographic separation (and only three), with firstly a separation step of the VARICOL™ type (in order to separate the first PUFA from the fourth fatty acid), and then a separation step of the CYCLOJET™ or HPLC type (in order to separate the first PUFA from the third fatty acid), and then a separation step of the VARICOL™ type (in order to separate the first PUFA from the second fatty acid).

According to one embodiment, the method according to certain aspects of the disclosure comprises three successive steps of chromatographic separation (and only three), with firstly a separation step of the VARICOL™ type (in order to separate the first PUFA from the fourth fatty acid), and then a separation step of the CYCLOJET™ or HPLC type (in order to separate the first PUFA from the third fatty acid), and then a separation step of the CYCLOJET™ or HPLC type (in order to separate the first PUFA from the second fatty acid).

When the method comprises two or more steps of chromatographic separation, these steps may be carried out simultaneously in physically separate units (of the same type or of different types and/or sizes), or may be carried out sequentially, in physically separate units or in the same units.

In addition, when two steps of chromatographic separation are carried out in an SMB or AMB type system, it is possible to implement them simultaneously on a same given AMB or SMB system. An example of simultaneous implementation on a same single apparatus is described in the WO 2011/080503 or in the WO 2013/005048 or in the WO 2013/005051, the disclosures of which are explicitly incorporated herein by reference in their respective entireties.

Thus, some separation units may be the same. For example, the first chromatographic unit 10 and the second chromatographic unit 6 may be the same unit; or the third chromatographic unit 3 and the second chromatographic unit 6 may be the same unit; or the first chromatographic unit 10 and the third chromatographic unit 3 may be the same unit; or the first chromatographic unit 10, the second chromatographic unit 6 and the third chromatographic unit 3 may be the same unit.

Alternatively, all of the chromatographic units may be separate units.

Each chromatographic separation step may be carried out on a reversed phase, as an adsorbent (stationary phase). For example, use may be made of adsorbents based on weakly polar resins or stationary phases based on silica chemically modified with organic groups such as alkyl groups (in particular C4, C8, C18, C24, C30 alkyl groups), phenyl groups, or others.

Each chromatographic separation step may be carried out using a water-organic eluent, that is to say, a mixture of one or more organic solvents with water. Preferably, all of the chromatographic separation steps are carried out using water-organic eluents. Alternatively, it is possible to implement some of the chromatographic separation steps with purely organic eluents.

The organic solvents that may be used in the context of the present disclosure (in particular for forming the water-organic eluents) are for example alcohols such as ethanol, propanol, isopropanol, and in a more preferred manner methanol; ketones such as acetone or methyl ethyl ketone; nitriles such as acetonitrile; esters such as methyl acetate or ethyl acetate; furans such as tetrahydrofuran; ethers such as diethyl ether or methyl ethyl ether; and combinations of two or more than two solvents from among these. Methanol and acetone are the preferred organic solvents.

Each water-organic eluent is characterised by a water/organic ratio, which is the volume ratio of water with respect to the organic solvent(s) in the eluent.

The water/organic ratio of each water-organic eluent may preferably vary from 0.01:99.99 to 30:70, and preferably from 5:95 to 25:75.

When the method comprises at least two chromatographic separation steps, these may be carried out with eluents having the same composition or different compositions.

It is preferred to use eluents having different compositions, and in particular having different water/organic ratios, this providing the ability to adjust the eluting strength of the eluent at each step of separation and thus to obtain the separation of different compounds in each step. It may also be desirable to use eluents consisting of various different organic solvents in different steps, in order to adjust the chromatographic selectivity between certain species to be separated at each separation step and thus to obtain the separation of different compounds at each step.

Preferably, the weight concentration of the first organic solvent eluent is controlled or adjusted to vary less than or equal to about 2%, preferably 1%, or 0.5%, or 0.2%, or 0.1%, above or below a predetermined target value; where appropriate preferably the weight concentration of the second organic solvent eluent is controlled or adjusted to vary less than or equal to about 2%, preferably 1%, or 0.5%, or 0.2%, or 0.1%, above or below a predetermined target value; where appropriate preferably the weight concentration of the third organic solvent eluent is controlled or adjusted to vary less than or equal to about 2%, preferably 1%, or 0.5%, or 0.2%, or 0.1%, above or below a predetermined target value. Control of the composition of eluents is performed by ensuring inflows of water and/or organic solvent(s) in order to make the necessary adjustments.

At the outlet of the first chromatographic unit 10, the stream enriched in the first PUFA may be the raffinate, and the stream enriched in the second fatty acid may be the extract; or conversely, the stream enriched in the first PUFA may be the extract, and the stream enriched in the second fatty acid may be the raffinate.

Accordingly, the second fatty acid may be less polar than the first PUFA, or conversely the second fatty acid may be more polar than the first PUFA.

At the outlet of the second chromatographic unit 6, the stream enriched in the first PUFA may be the raffinate, and the stream enriched in the third fatty acid may be the extract; or conversely, the stream enriched in the first PUFA may be the extract, and the stream enriched in the third fatty acid may be the raffinate.

Accordingly, the third fatty acid may be less polar than the first PUFA, or conversely the third fatty acid may be more polar than the first PUFA.

At the outlet of the third chromatographic unit 3, the stream enriched in the first PUFA may be the raffinate, and the stream enriched in the fourth fatty acid may be the extract; or conversely, the stream enriched in the first PUFA may be the extract, and the stream enriched in the fourth fatty acid may be the raffinate.

Accordingly, the fourth fatty acid may be less polar than the first PUFA, or conversely the fourth fatty acid may be more polar than the first PUFA.

According to one particular embodiment, the stream enriched in the first PUFA at the outlet of the third chromatographic unit 3 is the raffinate, the stream enriched in the first PUFA at the outlet of the second chromatographic unit 6 is the raffinate and the stream enriched in the first PUFA at the outlet of the first chromatographic unit 10 is the extract. Accordingly, the second fatty acid is more polar than the first PUFA, while the third fatty acid and the fourth fatty acid are less polar than the first PUFA.

Each stream (extract or raffinate) obtained from a chromatographic separation step is generally concentrated in order to eliminate the eluent (organic solvents and water) or to reduce the weight content of the organic solvents and water stream to a level of less than 10%, or less than 5%, or less than 2%, or less than 1%, or less than 0.5%, or less than 0.1%.

Thus, in one preferred embodiment, at least one concentration unit (not shown in the FIGURE) is associated with each chromatographic unit 3, 6, 10.

In particular, preferably, the stream enriched in the first PUFA collected upon completion of the chromatographic separation between the first PUFA and the second fatty acid is a concentrated stream (depleted of eluent or free or essentially free of organic solvents and water); similarly, where applicable, the stream enriched in the first PUFA collected following the chromatographic separation between the first PUFA and the third fatty acid, and the stream enriched in the first PUFA collected following the chromatographic separation between the first PUFA and fourth fatty acid are concentrated streams (depleted of eluent or free or essentially free of organic solvents and water); optionally, the stream enriched in the second fatty acid, and where applicable the stream enriched in the third fatty acid and the stream enriched in the fourth fatty acid are concentrated streams (depleted of eluent or free or essentially free of organic solvents and water).

In each concentration unit, the eluent may be evaporated and condensed, so as to separate it from the fatty acid mixture. Use may be made for example, of a falling film evaporator with recirculation, rising stream evaporator, a wiped film evaporator, a thin film evaporator, a thermosyphon evaporator, a rotary evaporator, a distillation column, a rectification column or any other evaporator or combination of evaporators that enable evaporation of the eluent and the concentration of the fatty acids concentrated at the base of the apparatus. Evaporation is preferably carried out at a pressure lower than atmospheric pressure, in particular at a pressure less than or equal to 750 mbar, or less than or equal to 500 mbar, or less than or equal to 300 mbar.

Alternatively, use may be made of a membrane separation device, with one or more separation stages, or a combination of evaporation means and membrane separation means.

The eluent evaporated and condensed, or otherwise separated, may be recycled to one or more steps of the process, in particular to one or more steps of chromatographic separation.

According to one embodiment, each concentration step (and in particular each step of concentration of the stream enriched in the first PUFA) may be carried out at a temperature less than or equal to 120° C., preferably less than or equal 100° C., preferably less than or equal to 90° C., preferably less than or equal to 80° C., less than or equal to 75° C.

According to one embodiment, each concentration step (and in particular each step of concentration of a stream enriched in the first PUFA) has a duration less than or equal to 6 hours, preferably less than or equal to 4 hours, preferably less than or equal to 3 hours, preferably less than or equal to 2 hours, preferably less than or equal to 1 hour and 30 minutes, preferably less than or equal to 1 hour.

According to particular embodiments, the eluent separated from the first stream enriched in the first PUFA (collected at the outlet of the first chromatographic separation unit 10) is more than 50% recycled, preferably more than 60% recycled, preferably more than 70% recycled, preferably more than 80% recycled, preferably more than 90% recycled, preferably more than 95% recycled, preferably more than 98% recycled, preferably more than 99% recycled.

According to particular embodiments, the eluent separated from the second stream enriched in the first PUFA (collected at the outlet of the second chromatographic separation unit 6) is more than 50% recycled, preferably more than 60% recycled, preferably more than 70% recycled, preferably more than 80% recycled, preferably more than 90% recycled, preferably more than 95% recycled, preferably more than 98% recycled, preferably more than 99% recycled.

According to particular embodiments, the eluent separated from the third stream enriched in the first PUFA (collected at the outlet of the third chromatographic separation unit 3) is more than 50% recycled, preferably more than 60% recycled, preferably more than 70% recycled, preferably more than 80% recycled, preferably more than 90% recycled, preferably more than 95% recycled, preferably more than 98% recycled, preferably more than 99% recycled.

According to particular embodiments, the eluent separated from the stream enriched in the second fatty acid is more than 50% recycled, preferably more than 60% recycled, preferably more than 70% recycled, preferably more than 80% recycled, preferably more than 90% recycled, preferably more than 95% recycled, preferably more than 98% recycled, preferably more than 99% recycled.

According to particular embodiments, the eluent separated from the stream enriched in the third fatty acid is more than 50% recycled, preferably more than 60% recycled, preferably more than 70% recycled, preferably more than 80% recycled, preferably more than 90% recycled, preferably more than 95% recycled, preferably more than 98% recycled, preferably more than 99% recycled.

According to particular embodiments, the eluent separated from the stream enriched in the fourth fatty acid is more than 50% recycled, preferably more than 60% recycled, preferably more than 70% recycled, preferably more than 80% recycled, preferably more than 90% recycled, preferably more than 95% recycled, preferably more than 98% recycled, preferably more than 99% recycled.

Preferably, the feedstock which is supplied at the inlet of each chromatographic separation unit and which is meant to be separated is as free as possible of solvents.

Thus:
- the initial mixture includes less than 80% of organic solvents; preferably less than 60%, or less than 40%, or less than 20%, or less than 10%, or less than 5%, or less than 2%, or less than 1% of organic solvents, and in a particularly more preferable manner, is a mixture of fatty acids essentially free of organic solvents; and/or
- where applicable, the third stream enriched in the first PUFA which feeds the second chromatographic separation unit 6 includes less than 80% of organic solvents; preferably less than 60%, or less than 40%, or less than 20%, or less than 10%, or less than 5%, or less than 2%, or less than 1% of organic solvents, and in a particularly more preferable manner, is a mixture of fatty acids essentially free of organic solvents; and/or
- where applicable, the second stream enriched in the first PUFA that feeds the first chromatographic separation unit 10 includes less than 80% of organic solvents, preferably less than 60%, or less than 40% or less than 20%, or 10% or less than 5%, or less than 2%, or less than 1% of organic solvents, and in a particularly more preferable manner, is a mixture of fatty acids essentially free of organic solvents.

Elimination of Oxygenated Compounds

In certain variations, the method provides for an elimination step for eliminating (or for reducing the amount of) oxygenated compounds after the chromatographic separation, or after the chromatographic separations.

Preferably, this step is not a step of chromatographic separation, and is not implemented in a chromatographic unit.

Preferably, this step does not separate the first PUFA from other fatty acids present in the stream (with the exception of oxygenated compounds such as peroxides and aldehydes).

The step of elimination of oxygenated compounds is carried out in the processing unit 14. This processing unit 14 may be in particular a molecular distillation unit or a short path evaporator. A short path evaporator is equipped with an internal condenser and can produce evaporation with a residence time of preferably less than 1000 s, preferably less than 100 s, preferably less than 10 s; at a pressure of preferably less than 10 mbar, preferably less than 1 mbar, preferably less than 0.1 mbar, preferably less than 0.01 mbar, preferably less than 0.001 mbar; at a temperature less than or equal to 200° C., preferably less than or equal to 150° C., preferably less than or equal to 120° C., preferably less than or equal to 100° C., preferably less than or equal to 80° C.

Alternatively, the processing unit 14 may be a unit for carrying out contacting with an adsorption substrate.

The adsorption substrate is any substrate capable of adsorbing oxygenated compounds such as peroxides and aldehyde compounds. It may for example be selected from among silica, alumina, activated carbon and derivatives thereof, in particular silica gels, silicates, aluminates and aluminosilicates. Clay such as bentonite is an example of a suitable substrate, similar to diatomaceous earth.

Adsorption may be carried out in a discontinuous process, that is to say a batch process, or in a continuous process, by percolation through an adsorbent bed. Preferably, the fatty acids are not diluted during this step, and in particular no solvent is added. The contacting process may last for example from 5 minutes to 24 hours, and in particular from 10 minutes to 10 hours, from 20 minutes to 5 hours, from 30 minutes to 2 hours, from 45 minutes to 1 hour and 30 minutes.

The amount of adsorbent used depends on the nature of the adsorbent and on its ability to capture the oxygenated compounds. It may for example be from 1 to 1000 g of adsorbent per kg of the stream to be processed (mixture of fatty acids), in particularly from 10 to 500 g/kg, more particularly from 25 to 200 g/kg.

At the end of the contacting phase, the adsorbent is separated from the mixture of fatty acids, and the latter may be filtered in order to prevent any contamination by the residual adsorbent.

Preferably, the binding of the oxygenated compounds to the adsorbent is essentially irreversible, that is to say, the adsorbent is not regenerated.

Alternatively, it is possible to regenerate the adsorbent, for example by heat treatment, in order to limit the volume and/or cost of treatment of waste.

The processing step of in the processing unit 14 may be used to reduce the peroxide value of the processed stream by at least 25%, preferably by at least 50%, preferably by at least 75%, preferably by at least 80%, or by at least 90%, or by at least 95%, or by at least 98%.

The processing step in the processing unit 14 may be used to reduce the anisidine value of the processed stream by at least 25%, preferably by at least 50%, preferably by at least 75%, preferably by at least 80%, or by at least 90%, or by at least 95%, or by at least 98%.

The peroxide value measures the amount of peroxide compounds in a mixture of fatty acids. The analytical method used is preferably as per European Pharmacopoeia, Section 2.5.5. Method A.

The anisidine value measures the amount of aldehyde compounds in a mixture of fatty acids. The analytical method used is preferably as per European Pharmacopoeia, Section 2.5.36.

According to one embodiment, the peroxide value of the stream resulting from the processing step (product collected in the purified first PUFA collection line 15) is less than or equal to 10, or less than or equal to 9, or less than or equal to 8, or less than or equal to 7, or less than or equal to 6, or less than or equal to 5, or less than or equal to 4 or less or equal to 3, or less than or equal to 2, or less than or equal to 1.5, or less than or equal to 1.

According to one embodiment, the anisidine value of the stream resulting from the processing step (product collected in the purified first PUFA collection line 15) is less than or equal to 20, or less than or equal to 18, or less than or equal to 16, or less than or equal to 14, or less than or equal to 12 or less than or equal to 10, or less than or equal to 9, or less than or equal to 8, or less than or equal to 7, or less than or equal to 6, or less than or equal to 5, or less than or equal to 4, or less than or equal to 3, or less than or equal to 2.

Another processing step analogous to that described above, and more particularly a step of molecular distillation, may also be provided for upstream, in particular prior to any chromatographic separation step.

In certain aspects, the initial mixture, upstream of the liquid phase chromatographic separation step or steps, has a predetermined peroxide value required per specifications for the purified first polyunsaturated fatty acid. Thus according to one embodiment, such a peroxide value of the initial mixture, which is subjected to the chromatographic separation process or processes, is less than or equal to 10, or less than or equal to 9, or less than or equal to 8, or less than or equal to 7, or less than or equal to 6, or less than or equal to 5, or less than or equal to 4, or less than or equal to 3, or less than or equal to 2, or less than or equal to 1.5, or less than or equal to 1.

In certain aspects, the initial mixture, upstream of the liquid phase chromatographic separation step or steps, has a predetermined anisidine value required per specifications for the purified first polyunsaturated fatty acid. Thus according to one embodiment, such an anisidine value of the initial mixture, which is subjected to the chromatographic separation process or processes, is less than or equal to 20, or less than or equal to 18, or less than or equal to 16, or less than or equal to 14, or less than or equal to 12, or less than or equal to 10, or less than or equal to 9, or less than or equal to 8, or less than or equal to 7, or less than or equal to 6, or less than or equal 5, or less than or equal to 4, or less than or equal to 3, or less than or equal to 2.

The inventors have found that the peroxide value and/or the anisidine value increases in the steps of chromatographic separation described here above, when the first PUFA is separated from compounds that are more apolar than itself, and this is so although the conditions of chromatographic separation are mild conditions—the chromatographic separations are in particular carried out in the absence of oxygen and protected from light, and/or at a moderate temperature. Without wanting to be bound by a theory, the inventors believe that this increase may be due in particular to the use of water-organic eluents.

According to one embodiment, the peroxide value of the stream containing the first PUFA increases during the step of chromatographic separation between the first PUFA and the second fatty acid (that is to say between the fatty acid mixture feeding line 9 and the line of stream enriched in the first PUFA 12), preferably by at least 30%, or by at least 50%, or by at least 75%, or by at least 100%, or by at least 150%, or by at least 200%, or by at least 300%, or by at least 500%.

According to one embodiment, the anisidine value of the stream containing the first PUFA increases during the step of chromatographic separation between the first PUFA and the second fatty acid (that is to say between the fatty acid mixture feeding line 9 and the line of stream enriched in the first PUFA 12), preferably by at least 30%, or by at least 50%, or by at least 75%, or by at least 100%, or by at least 150%, or by at least 200%, or by at least 300%, or by at least 500%.

According to one embodiment, the peroxide value of the stream containing the first PUFA increases during the step of chromatographic separation between the first PUFA and the third fatty acid (that is to say between the fatty acid mixture feeding line 5 and the line of stream enriched in the first PUFA 9), preferably by at least 30%, or by at least 50%, or by at least 75%, or by at least 100%, or by at least 150%, or by at least 200%, or by at least 300%, or by at least 500%.

According to one embodiment, the anisidine value of the stream containing the first PUFA increases during the step of chromatographic separation between the first PUFA and the third fatty acid (that is to say between the fatty acid mixture feeding line 5 and the line of stream enriched in the first PUFA 9), preferably by at least 30%, or by at least 50%, or by at least 75%, or by at least 100%, or by at least 150%, or by at least 200%, or by at least 300%, or by at least 500%.

According to one embodiment, the peroxide value of the stream containing the first PUFA increases during the step of chromatographic separation between the first PUFA and the fourth fatty acid (that is to say between the fatty acid mixture feeding line 1 and the line of stream enriched in the first PUFA 5), preferably by at least 30%, or by at least 50%, or by at least 75%, or by at least 100%, or by at least 150%, or by at least 200%, or by at least 300%, or by at least 500%.

According to one embodiment, the anisidine value of the stream containing the first PUFA increases during the step of chromatographic separation between the first PUFA and the fourth fatty acid (that is to say between the fatty acid mixture feeding line 1 and the line of stream enriched in the first PUFA 5), preferably by at least 30%, or by at least 50%, or by at least 75%, or by at least 100%, or by at least 150%, or by at least 200%, or by at least 300%, or by at least 500%.

According to one embodiment, the peroxide value of the stream enriched in the first PUFA resulting from the chromatographic separation of the first PUFA and of the second fatty acid (that is to say emerging from the first chromatographic unit 10) is greater than the peroxide value of the initial mixture (that is to say the mixture that is possibly preprocessed which is meant to be subjected to the step or steps or chromatographic separation), preferably by at least 30%, or by at least 50%, or by at least 75%, or by at least 100%, or by at least 150%, or by at least 200%, or by at least 300%, or by at least 500%.

According to one embodiment, the anisidine value of the stream enriched in the first PUFA resulting from the chromatographic separation of the first PUFA and of the second fatty acid (that is to say emerging from the first chromatographic unit 10) is greater than the anisidine value of the initial mixture (that is to say the mixture that is possibly preprocessed which is meant to be subjected to the step or steps or chromatographic separation), preferably by at least 30%, or by at least 50%, or by at least 75%, or by at least 100%, or by at least 150%, or by at least 200%, or by at least 300%, or by at least 500%.

In the event where one of the chromatographic separations carried out has not had the consequence of significantly increasing the peroxide value or the anisidine value of the stream of interest, it is possible to reverse the order of steps, that is to say, to carry out this or these chromatographic separation step or steps after the step of reduction of the peroxide value/the anisidine value.

Thus, in the case in point, one may envisage for example:

a step of chromatographic separation of the first PUFA and the second fatty acid, followed by a processing step comprising reducing the peroxide value and/or the anisidine value of the stream enriched in the first PUFA, followed by a step of chromatographic separation of the first PUFA and the third fatty acid; or a step of chromatographic separation of the first PUFA and the third fatty acid, followed by a step of chromatographic separation of the first PUFA and the second fatty acid, followed by a processing step comprising reducing the peroxide value and/or the anisidine value of the stream enriched in the first PUFA, followed by a step of chromatographic separation of the first PUFA and the fourth fatty acid; or a step of chromatographic separation of the first PUFA and the second fatty acid, followed by a processing step comprising reducing the peroxide value and/or the anisidine value of the stream enriched in the first PUFA, followed by a step of chromatographic separation of the first PUFA and the fourth fatty acid, followed by a step of chromatographic separation of the first PUFA and the third fatty acid.

The method may include a step of addition of a stabiliser (antioxidant), such as tocopherol, ascorbic acid or any other compound or mixture of compounds known to the person skilled in the art, in order to prevent degradation of the product and a further increase in the peroxide value or anisidine value. This step of addition of the stabiliser is preferably carried out at the end of the process, after all the chromatographic separation steps and after the processing step.

Product

According to one embodiment, the first PUFA is an omega-3 fatty acid.

According to various different embodiments, the first PUFA may be eicosapentaenoic acid (EPA), or docosahexaenoic acid (DHA), or arachidonic acid (ARA), or docosapentaenoic acid (DPA), or stearidonic acid (SDA).

According to one embodiment, the first PUFA is EPA and the second fatty acid is DHA.

According to one embodiment, the first PUFA is DHA and the second fatty acid is EPA.

According to one embodiment, the first PUFA is EPA and the second fatty acid is SDA.

According to one embodiment, the first PUFA is SDA and the second fatty acid is EPA.

According to one embodiment, the first PUFA is the DPA and the second fatty acid is DHA.

According to one embodiment, the first PUFA is DHA and second fatty acid is DPA.

According to one embodiment, the first PUFA is ARA and second fatty acid is DHA.

According to one embodiment, the first PUFA is DHA and second fatty acid is ARA.

According to one embodiment, the first PUFA is EPA, the second fatty acid is DHA or SDA, and the third fatty acid and the fourth fatty acid are selected from the one of DHA and SDA which is not the second fatty acid, and from among saturated fatty acids and monounsaturated fatty acids.

The concentration of the first PUFA in the final product obtained at the end of the process (collected in the purified first PUFA collection line 15) may be greater than or equal to about 80%, preferably greater than or equal to about 90%, or greater than or equal to about 95%, or greater than or equal to about 97%, or greater than or equal to about 98%, or greater than or equal to about 99% (relative to the total of fatty acids).

The concentration of the second fatty acid in this final product may be less than or equal to about 1%, or less than or equal to about 0.1%, or less than or equal to about 0.05%, or less than or equal to about 0.03%, or less than or equal to about 0.01% (relative to the total of fatty acids).

The concentration of the third fatty acid in this final product may be less than or equal to about 1%, or less than or equal to about 0.1%, or less than or equal to about 0.05%, or less than or equal to about 0.03%, or less than or equal to about 0.01% (relative to the total of fatty acids).

The concentration of the fourth fatty acid in this final product may be less than or equal to about 1%, or less than or equal to about 0.1%, or less than or equal to about 0.05%, or less than or equal to about 0.03%, or less than or equal to about 0.01% (relative to the total of fatty acids).

For example, the final product obtained at the end of the process (collected in the purified first PUFA collection line 15) may contain EPA in a proportion greater than or equal to about 80%, or greater than or equal to about 95%, or greater than or equal to about 97%, or greater than or equal to about 98%, or greater than or equal to about 99% (relative to the total of fatty acids); as well as DHA in a proportion less than or equal to about 1%, or less than or equal to about 0.1%, or less than or equal to about 0.05%, or less than or equal to about 0.03% or less than or equal to about 0.01%.

The oil enriched in the first PUFA is preferably stored in an environment protected from air and light prior to the packaging and/or use thereof, including for example the final formulation and/or encapsulation.

According to one embodiment, the final product is combined with a pharmaceutically and/or dietetically acceptable carrier and/or excipients and/or diluents. This product may thus be formulated for example in the form of hard capsules or caplets, capsules or tablets (or in any other form suitable for oral or parenteral or topical administration).

Each individual dosage form (for example capsule or hard capsule/caplet) may contain for example from 250 to 1500 mg, preferably from 300 to 1000 mg of the above mentioned product.

The product may thus be used for the preparation of a pharmaceutical composition for the prevention and/or the treatment and/or the prophylaxis of the risk factors for cardiovascular diseases, such as hypertriglyceridemia, hypercholesterolemia and hypertension; and for cardiovascular diseases such as arrhythmia, atrial and/or ventricular fibrillation, cardiac failure and cardiac decompensation; for the primary and secondary prevention of myocardial infarction and reinfarction; for the treatment of any other pathological conditions that may possibly be treated by the above mentioned PUFAs, such as autoimmune diseases, ulcerative colitis, tumour pathologies, nervous system illnesses, cell aging, cerebral infarct, ischemic diseases, and psoriasis, for example.

Alternatively, the product may be used in parapharmaceutical applications, and especially dietetic uses, in particular in infant nutrition.

EXAMPLES

The following example illustrates the certain aspects of the present teachings of the disclosure without limitation thereof.

In this example, ethyl ester of EPA with a purity of more than 96% has been obtained by means of three successive chromatography steps, from a mixture of ethyl esters containing more than 50% of EPA, and having a peroxide value of 4.5 and an anisidine value of 11.

All of the chromatography operations are carried out under inert atmosphere conditions and protected from light.

All of the chromatography operations are carried out on a VARICOL™ type chromatography system, with five columns that are 20 cm in diameter, filled with a stationary phase of C18 reversed phase silica. The chromatography system is coupled with two falling film evaporators with recirculation, for the concentration of the extract and the raffinate, respectively.

The conditions for chromatography and evaporation are as follows:

Step 1:
eluent: acetone/water in a ratio of 90/10 v/v;
complete evaporation of the eluent from the raffinate (target product) at 250 mbar and 75° C.;
complete evaporation of the eluent from the extract at 250 mbar and 75° C.

The concentrated raffinate contains EPA in a proportion of about 70% (surface area measurement by gas chromatography) and less than 1% of residual solvents. The average peroxide value obtained is 8.0 and the average anisidine value obtained is 13.8.

Step 2:
eluent: methanol/water in a ratio of 93/7 v/v;
complete evaporation of the eluent from the raffinate (target product) at 250 mbar and 75° C.,
partial evaporation of the eluent from the extract at 1000 mbar and 75° C.

The concentrated raffinate contains EPA in a proportion of about 92% (surface area measurement by gas chromatography) and less than 1% of residual solvents. The average peroxide value obtained is 7.4 and the average anisidine value obtained is 22.6.

Step 3:
eluent: acetone/water in a ratio of 79/21 v/v;
complete evaporation of the eluent from the raffinate at 250 mbar and 75° C.;
complete evaporation of the eluent from the extract (target product) at 250 mbar and 75° C.

The concentrated extract contains EPA in a proportion of about 97% (surface area measurement by gas chromatography) and less than 1% of residual solvents. The average peroxide value obtained is 6.5 and the average anisidine value obtained is 6.1.

A final step of nitrogen stripping and elimination of the oxidation compounds is carried out in a discontinuous batch process under the following conditions:
stripping by bubbling nitrogen at 75° C. for 1 hour;
addition of 100 g of bentonite per kg of oil, stirring under vacuum at 50 mbar for 1 hour;
filtration.

An antioxidant (tocopherol 0.2%) is added. The peroxide value and the anisidine value in the purified EPA are measured to be between 0.6 and 0.7 and between 1.0 and 2.6 respectively.

What is claimed is:

1. A method for purification of a first polyunsaturated fatty acid from an initial mixture, the initial mixture comprising at least one second fatty acid in addition to the first polyunsaturated fatty acid, the method comprising:
separating the initial mixture via at least one step of chromatographic separation in liquid phase of the first polyunsaturated fatty acid and the second fatty acid to recover a first stream enriched in the first polyunsaturated fatty acid, and a second stream enriched in the second fatty acid; and processing the first stream enriched in the first polyunsaturated fatty acid to decrease a peroxide value and/or an anisidine value of the first stream.

2. The method of claim 1, wherein the processing is a step of molecular distillation.

3. The method of claim 1, wherein the processing is a step of contacting with an adsorption substrate.

4. The method of claim 1, wherein after the processing, the peroxide value of the first stream enriched in the first polyunsaturated fatty acid is less than or equal to 2 and/or the anisidine value of the first stream enriched in the first polyunsaturated fatty acid is less than or equal to 10.

5. The method of claim 1, wherein the first polyunsaturated fatty acid is eicosapentaenoic acid and is recovered after the processing with a purity greater than or equal to 90%.

6. The method of claim 1, wherein the separating the initial mixture via at least one step of chromatographic separation of the first polyunsaturated fatty acid and of the second fatty acid is implemented with a water-organic eluent.

7. The method of claim 1, wherein the second fatty acid is a polyunsaturated fatty acid.

8. The method of claim 1, wherein the initial mixture further comprises a third fatty acid, and the method includes a step of liquid phase chromatographic separation of the first polyunsaturated fatty acid and of the third fatty acid, to recover a third stream enriched in the first polyunsaturated fatty acid and a fourth stream enriched in the third fatty acid.

9. The method of claim 8, wherein the initial mixture further comprises a fourth fatty acid, and the method includes a step of liquid phase chromatographic separation of the first polyunsaturated fatty acid and of the fourth fatty acid, to recover a fifth stream enriched in the first polyunsaturated fatty acid and a sixth stream enriched in the fourth fatty acid.

10. The method of claim 9, wherein the separating of the initial mixture successively comprises (i) the step of liquid phase chromatographic separation of the first polyunsaturated fatty acid and of the fourth fatty acid, the first polyunsaturated fatty acid being less retained than the fourth fatty acid, and then (ii) the step of liquid phase chromatographic separation of the first polyunsaturated fatty acid and the third fatty acid, the first polyunsaturated fatty acid being less retained than the third fatty acid, and then (iii) the step of liquid phase chromatographic separation of the first polyunsaturated fatty acid and the second fatty acid, the first polyunsaturated fatty acid being more retained than the second fatty acid.

11. The method of claim 1, wherein the first polyunsaturated fatty acid is less retained than the second fatty acid during the step of chromatographic separation of the first polyunsaturated fatty acid and of the second fatty acid.

12. The method of claim 1, including a preliminary processing step to decrease the peroxide value and/or the anisidine value relative to the initial mixture, upstream of the separating of the initial mixture via the liquid phase chromatographic separation step or steps.

13. The method of claim 1 wherein upstream of the separating of the initial mixture via the liquid phase chromatographic separation step or steps, the initial mixture has a predetermined peroxide value and a predetermined anisidine value required for the purified first polyunsaturated fatty acid.

14. The method of claim 1, wherein the peroxide value of the initial mixture is less than or equal to 10 and/or the anisidine value of the initial mixture is less than or equal to 15.

15. The method of claim 1, wherein the second fatty acid is more polar than the first polyunsaturated fatty acid.

16. The method of claim 1, wherein the first polyunsaturated fatty acid is eicosapentaenoic acid and after the separating, said first stream contains at least 96 wt. % eicosapentaenoic acid.

17. A method for purification of a first polyunsaturated fatty acid from an initial mixture of fatty acids, wherein the method successively comprises:

providing a stream from the initial mixture;

enriching the stream in the first polyunsaturated fatty acid in at least one step of chromatographic separation in liquid phase, wherein said stream has a peroxide value and/or an anisidine value which is higher after said step of chromatographic separation than before said step of chromatographic separation; and processing the stream to decrease the peroxide value and/or the anisidine value of the stream.

18. The method of claim 17, wherein the processing step is selected from a step of molecular distillation and a step of contacting with an adsorption substrate.

19. The method of claim 17, wherein the at least one step of chromatographic separation is performed using a water-organic eluent.

20. The method of claim 17, wherein the method comprises enriching the stream in the first polyunsaturated fatty acid in at least two steps of chromatographic separation in liquid phase.

21. The method of claim 17, wherein the method comprises enriching the stream in the first polyunsaturated fatty acid in at least three steps of chromatographic separation in liquid phase.

22. The method of claim 17, wherein the method successively comprises:

providing the stream from the initial mixture;

enriching the stream in the first polyunsaturated fatty acid in a first step of chromatographic separation in liquid phase, wherein the peroxide value and/or the anisidine value of the stream is higher after the first step of chromatographic separation than before the first step of chromatographic separation;

enriching the stream in the first polyunsaturated fatty acid in a second step of chromatographic separation in liquid phase, wherein the peroxide value and/or the anisidine value of the stream is higher after the second step of chromatographic separation than before the second step of chromatographic separation;

enriching the stream in the first polyunsaturated fatty acid in a third step of chromatographic separation in liquid phase, wherein the peroxide value and/or the anisidine value of the stream is lower after the third step of chromatographic separation than before the third step of chromatographic separation; and processing the stream to decrease the peroxide value and/or anisidine value of this stream.

23. The method of claim 17, wherein the first polyunsaturated fatty acid is eicosapentaenoic acid and after the processing, said stream contains at least 96 wt. % eicosapentaenoic acid.

24. A method for purification of a first polyunsaturated fatty acid from an oil, wherein the oil has a peroxide value of less than 10 and an anisidine value of less than 15, and wherein the method successively comprises:

providing a stream from the initial mixture;

enriching the stream in the first polyunsaturated fatty acid in at least one step of chromatographic separation in liquid phase; and processing the stream to decrease the peroxide value and/or the anisidine value of the stream.

25. The method of claim 24, wherein the processing step is selected from a step of molecular distillation and a step of contacting with an adsorption substrate.

26. The method of claim 24, wherein the method comprises enriching the stream in the first polyunsaturated fatty acid in a sequence of at least two steps of chromatographic separation in liquid phase, wherein said sequence comprises at least a first step of chromatographic separation and a last step of chromatographic separation.

27. The method of claim 26, wherein the peroxide value of the stream before the first step of chromatographic separation in liquid phase is lower than the peroxide value of the stream after the last step of chromatographic separation in liquid phase.

28. The method of claim 26, wherein the anisidine value of the stream before the first step of chromatographic separation in liquid phase is lower than the anisidine value of the stream after the last step of chromatographic separation in liquid phase.

29. The method of claim 24, wherein the first polyunsaturated fatty acid is eicosapentaenoic acid and after the processing, said stream contains at least 96 wt. % eicosapentaenoic acid.

* * * * *